United States Patent [19]

Kambara

[11] 4,144,451
[45] Mar. 13, 1979

[54] MASS SPECTROMETER

[75] Inventor: Hideki Kambara, Kodaira, Japan

[73] Assignee: Hitachi, Ltd., Japan

[21] Appl. No.: 762,718

[22] Filed: Jan. 26, 1977

[30] Foreign Application Priority Data

Jan. 28, 1976 [JP] Japan .................................. 51-7500

[51] Int. Cl.$^2$ ........................................... B01D 59/44
[52] U.S. Cl. .................................. 250/281; 250/289; 250/427; 250/457
[58] Field of Search ................. 250/281, 457, 427, 289

[56] References Cited

U.S. PATENT DOCUMENTS

| 3,920,987 | 11/1975 | Anbar et al. | 250/281 |
| 4,023,398 | 5/1977 | French et al. | 250/281 |

Primary Examiner—Harold A. Dixon
Attorney, Agent, or Firm—Craig & Antonelli

[57] ABSTRACT

Herein disclosed is an atmospheric pressure ionization mass spectrometer having a mediate pressure region, wherein a jet separator is incorporated for playing a double role of differential pumping and concentration of the electric field, and wherein a gas jetting aperture of the jet separator and another aperture for introducing a gas to an analyzing region of the spectrometer are made of a conductive body and are adapted to be kept at different electric potentials.

11 Claims, 9 Drawing Figures

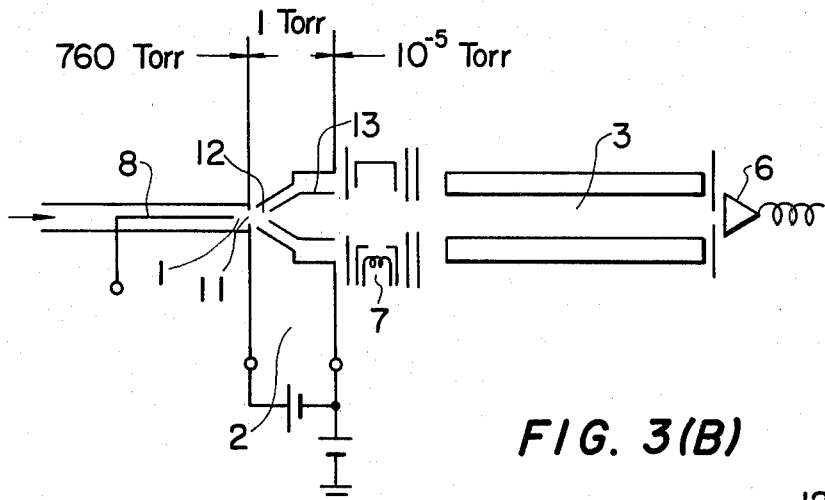
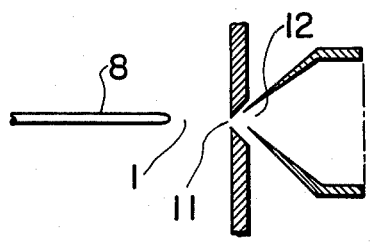
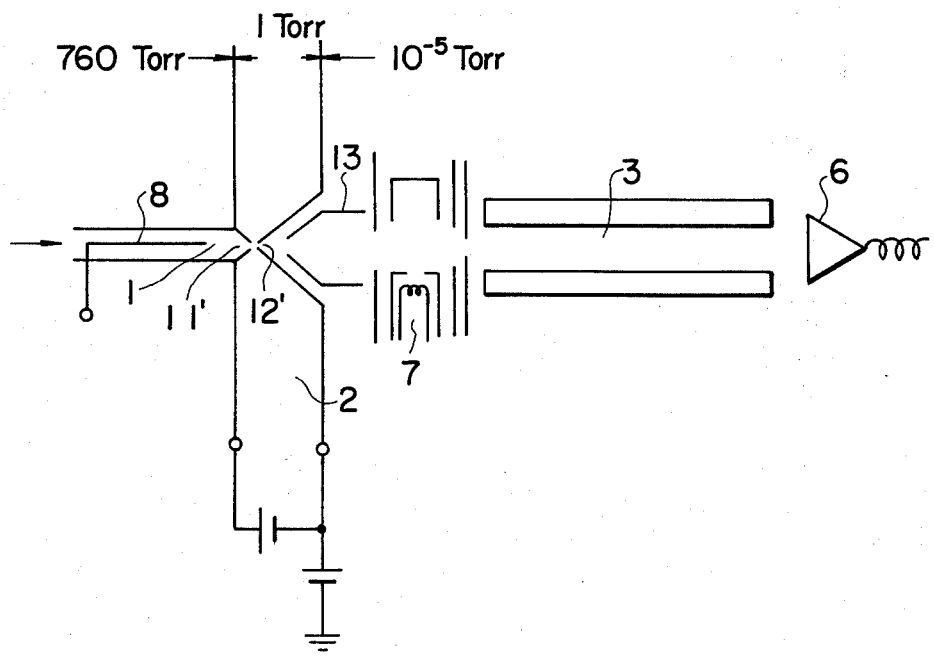

MASS SPECTROMETER

BACKGROUND OF THE INVENTION

The present invention relates to a mass spectrometer and, more particularly, to an improvement in those mass spectrometers which have functions of electron impact ionization (EI) and atmospheric pressure ionization (API).

Recently, a remarkable progress has been made in trace-impurities analyses of gases, which consists of efficiently ionizing a sample at an atmospheric pressure and introducing the resulting ions into a mass spectrometer through a fine aperture.

By way of reference material, analyzing methods of the above mentioned kind have been described in articles entitled "New Picogram Detection System Based on a Mass Spectrometer with an External Ionization Sources at Atmospheric Pressure" by E. C. Horning et al. (Analytical Chemistry, Vol. 45, No. 6, May 1973), and in "Subpicogram Detection System for Gas Phase Analysis Based upon Atmospheric Pressure Ionization (API) Mass Spectrometry" by E. C. Horning et al. (Analytical Chemistry, Vol. 46, No. 6, May 1974), as well as in the specification of Japanese Patent Application No. 78293/1974 entitled "Atmospheric Ionization Mass Spectrometer", filed by the present inventors. In these methods, primary ions are generated by a radioisotope or by an electric discharge and then a sample is ionized by ion molecule reactions. Thus, these methods are superior to other conventional methods employing electron impact ionization in that they can afford an ionization efficiency higher by about one figure than those provided by the other methods thereby to ensure higher sensitivity and provide a simpler spectrum which is easy to read, due to less decomposition of the sample.

Referring to FIG. 1 which shows a conventional atmospheric pressure ionization mass spectrometer having a radioisotope as means for effecting the ionization, a sample is efficiently ionized in an ionization region 1, by ion molecule reactions with a radioisotope 5 or with reactant ions generated by the radioisotope 5.

The ion molecule reactions are considered to take place in the following process. In general, the sample reaches the ionization region while it being suspended or contained by a carrier gas such as $N_2$, $O_2$, Ar or air. In the ionization region, the carrier gas is ionized by the radioisotope and the resultant ions produce an ion molecule reaction with water remaining in the carrier gas to produce reactant ions such as $H_2O^+$ or $(H_2O)_n H^+$. Then, the reactant ions perform an ion molecule reaction with the trace amounts of molecules to be detected to ionize the latter. The generated ions are introduced through a fine aperture 4 into a mass spectrometric analysis region 3 in which a high vacuum is established. The analysis is carried out in this region by means of a quadrupole mass spectrometer or a spectrometer employing a sector magnetic field and is finally detected by a detector 6. An EI ion source for mass calibration 7 which is an electron impacting source in the illustrated arrangement is disposed at the upstream side of the mass spectrometric analysis region 3.

In this known arrangement, a normal electron impact ionization spectrum is not obtained because the sample-carrying gas necessarily passes through the ionization region 1 where the radioisotope 5 is located. In addition, since the differential pumping is performed through only one fine aperture 4, it is necessary to make the diameter of the aperture small for example, 20μm, so that the clogging of the aperture or other troubles are likely to occur.

In the atmospheric ionization, only molecules having a low ionization potential and molecules which tend to be ionized by the addition of $H^+$ are selectively ionized with high efficiency through the ion molecule reaction, while substances having a high ionization potential and substances which are less likely to be ionized by the $H^+$ addition are not kept ionized even when the carrier gas is rich in such substances. Therefore, it is not possible to make the best use of the high sensitivity of API if only atmospheric pressure ionization is used solely. A combination of the atmospheric pressure ionization with the electron impact ionization is preferred.

FIG. 2 shows an arrangement which is also a conventional one but improved to overcome the above described problems. The ionization by radioisotope is replaced by an ion source using a corona discharge, while two-stage differential pumping is adopted to allow use of a larger diameter fine aperture.

Referring to FIG. 2, an electrode 8 for the corona discharge is effective to cause an ionization and anion molecule reaction in the ionization region 1. The ions of the molecules to be measured pass through the aperture 4 to a mediate pressure region 2 which is evacuated to about 1 Torr by means of evacuation means (now shown). Since the ion molecule reaction takes place also in this mediate pressure region, this region 2 may be referred to as an ion molecule reaction region. The ions are then introduced into the mass spectral region 3, through a second fine aperture 9.

The diameters of the first and the second fine apertures 4 and 9 are, for example, 100μm and 200μm, respectively. The mediate pressure region 2 is provided with ion focusing auxiliary electrodes 10 for producing a electric field effective to converge and focus the ions on the second aperture 9. In this arrangement, it is possible to alternately conduct an analysis by atmospheric pressure ionization and an analysis by ionization by another means, such as electron impact ionization at the upstream side of the mass spectral region. This means that all kinds of gases may be conveniently ionized to be analyzed, without deteriorating the sensitivity in analyzing molecules having a low ionization potential and molecules which are more likely to be ionized by addition of $H^+$ (proton transfer). The adoption of two-stage differential pumping allows the use of a larger fine aperture, which conveniently ensures that the problem of clogging of the aperture will be avoided.

However, this improved arrangement disadvantageously requires provision of a plurality of ion focusing auxiliary electrodes in the mediate pressure region 2. In addition, this arrangement is not effective as a separator, when used in the electron impact ionizing mode, since no substantial concentration of heavy molecule is expected as the molecules travel from the sample gas inlet port to the ion source located at the upstream side of the mass spectral region. To explain this in more detail, when the arrangement of FIG. 2 utlizes electron impact ionization, the density of the molecules to be measured at the ionization region is as low as that at the gas inlet port, so that the analyzing sensitivity is insufficiently low, although the arrangement is apparently designed to perform the electron impact ionizing function.

In order to overcome this problem, it has been proposed to adopt a jet separator which has been commonly used in combining a gas chromatograph with a mass spectrometer (GC-MS). The jet separator is usually capable of injecting a sample from a gas chromatograph working almost at atmospheric pressure to a mass spectrometer working at a vacuum of about $10^{-5}$ Torr. In addition, the jet separator is capable of selectively injecting a heavier sample carried by a lighter carrier such as He, owing to the radial diffusion velocity differential of the jetted molecules, which differential is attributable to the difference in weights of the molecules, thus effecting the "concentration" of the sample.

This solution in which the jet separator is found, however, is also inconvenient in that ionized molecules are hardly injected into the mass spectrometer when the apparatus is used in the atmospheric pressure ionization mode.

SUMMARY OF THE INVENTION

It is therefore an object of the invention to provide an improved mass spectrometer capable of performing a trace-impurities analyses of gases.

It is another object of the invention to provide an improved mass spectrometer capable of performing the double functions of atmospheric pressure ionization analysis and electron impact ionization analysis, the latter ionization being made at the upstream side of a mass spectral region.

It is still another object of the invention to provide an improved mass spectrometer incorporating a jet separator.

These and other objects of the invention have been accomplished by the mass spectrometer of the invention in which a jet separator intended for concentration of heavy gas molecules is adapted to play the additional roles of differential pumping and electric field concentration, and in which the gas jetting fine aperture of the jet separator and the gas introducing fine apertures are made of conductive materials, while means are provided for applying an electric potential between the apertures.

BRIEF DESCRIPTION OF THE DRAWINGS

FIG. 3A is a schematic section of a mass spectrometer which is an embodiment of the present invention.

FIG. 3B is a partial sectional view of the embodiment of the present invention.

FIGS. 4, 5 and 6 are schematic illustrations of different embodiments of the present invention.

DETAILED DESCRIPTION OF THE PREFERRED EMBODIMENTS

Figure 1:
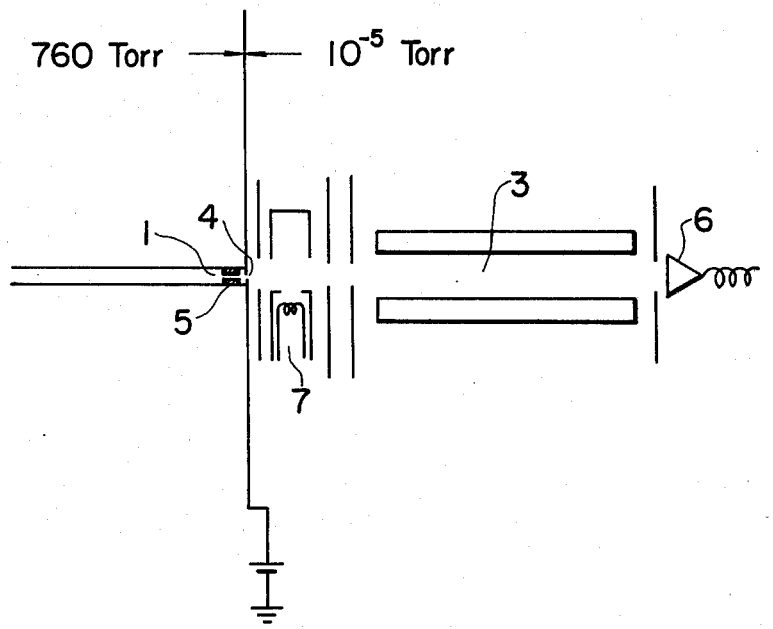
FIG. 1 is a schematic section of a conventional atmospheric pressure ionization mass spectrometer having a radioisotope.
Figure 2:
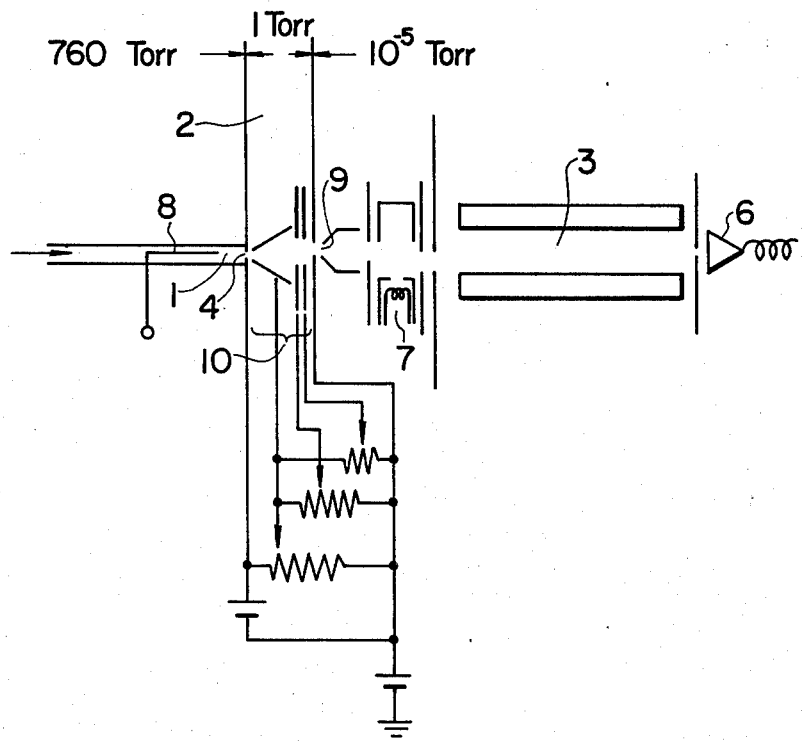
FIG. 2 is a schematic illustration of a conventional atmospheric pressure ionization mass spectrometer incorporating a two-stage differential pumping.

According to the invention, an ionization at the upstream side of the mass spectral region is advantageously combined with an atmospheric ionization in one mass spectrometer. Thus, for the ionization of molecules having a high ionization potential or molecules which are hard to ionize, auxiliary ionization means are provided at the upstreamside of the mass spectrometric analysis region for cooperation with the jet separator which is effective to concentrate the molecules to perform a highly sensitive detection, while substances having a low ionization potential and substances which are more likely to perform ion molecule reactions are ionized by means of the atmospheric pressure ionizoation which promises a high analytical sensitivity. The high sensitivity is ensured also by an application of an electrical potential between the gas jetting fine aperture of the jet separator and the gas introducing fine aperture, which potential is effective to concentrate ions forwarded from the ionization region to the mass spectrometric analysis region.

Thus, according to the invention, there is provided a mass spectrometer characterized by an ionization region, a mediate pressure region and a mass spectrometric analysis region having at its upstream side auxiliary ionization means, said ionization region and said mediate pressure region being separated from each other by a partition wall at least a part of which is made of a conductive material to form a first electrode, a fine aperture formed in said first electrode for intercommunication of said ionization region and said mediate pressure region, said mediate pressure region and said mass spectrometric analysis region being separated from each other by another partition wall at least a portion of which is made of a conductive material to form a second electrode, said second electrode also having a fine aperture formed therein for intercommunication of said mediate pressure region and said mass spectrometric analysis region, said fine apertures in combination constituting a jet separator and being connected to receive an electric potential therebetween.

The invention will be more fully understood from the following description of embodiments taken in conjunction with the drawings.

Referring to FIG. 3 showing a mass spectrometer embodying the present invention, a gas jetting fine aperture 11 and a gas introducing fine aperture 12 are formed in respective electrodes of a conductive material or materials which are electrically insulated from each other, so that an electric potential may be applied therebetween. Both fine apertures 11 and 12 are disposed to oppose to each other with a certain gap of about 1 mm therebetween, so as to constitute a jet separator in combination with each other. In the illustrated embodiment, the diameters of the gas jetting and gas introducing fine apertures 11, 12 are 60$\mu$m and 200$\mu$m, respectively. The fine apertures define trapezoidal cross-sections having apex angles of 90°, respectively, as shown in FIG. 3B. The gas jetting fine aperture 11 and the gas introducing fine aperture 12 may be made of stainless steel ion-plated with gold.

The interface functions as a jet separator, when a spectrum of ions ionized by an electron impact ion source is to be measured. The electron impact ion source is located at the upstream side of a mass spectrometric analysis region 3 and constitutes auxiliary ionization means 7. For measuring a spectrum produced by atmospheric pressure ionization, an electric potential of, for example, several volts is applied between the fine apertures 11 and 12.

The ions generated by corona discharge and by the subsequent ion molecule reactions are induced into a mediate pressure region 2, through the gas jetting fine aperture 11, and are accelerated in the axial direction by the electric field applied to the mediate pressure region 2. Consequently, the flow rate of ions taken into the highly evacuated region through the gas introducing fine aperture 12 is much increased as compared with the case where no electric field is applied. This concentration afforded by the electric field ensures an analysis sensitivity as high as is the case of the conventional arrangement, and, in addition, the electric field is effective also in concentrating neutral sample molecules which are introduced to be ionized by the auxiliary ionization means 7. Namely, when the electron ionization means 7, i.e. the auxiliary ionization means 7 is used for the ionization of samples, the electric field is effective to concentrate the sample to be ionized, while, when atmospheric pressure ionization is used, the produced ions are concentrated by the electric field to be sent to the mass spectral region 3.

When the mass spectrometer of this embodiment is used in combination with a gas chromatograph, the output from the gas chromatograph is introduced to the ionization region 1.

Figure 5:
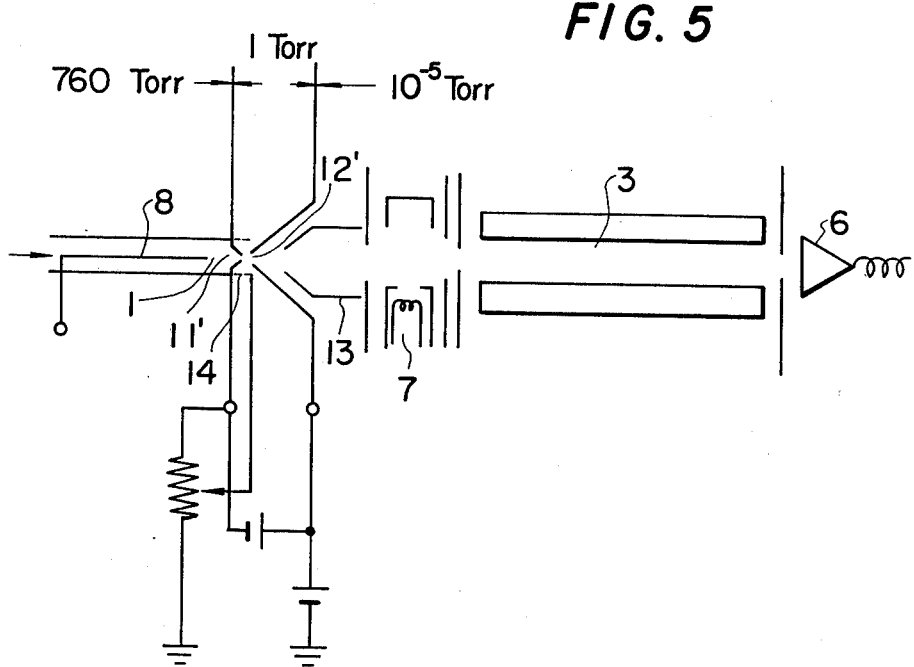

Referring to FIG. 4 which shows a modification, the gas jetting fine aperture and the gas introducing fine aperture are formed of conical electrodes 11' and 12', the cones being disposed to oppose to each other at their converging ends. In another modification as shown in FIG. 5, a mesh electrode 14 is employed for enhancing the ion-focusing efficiency.

Figure 6:
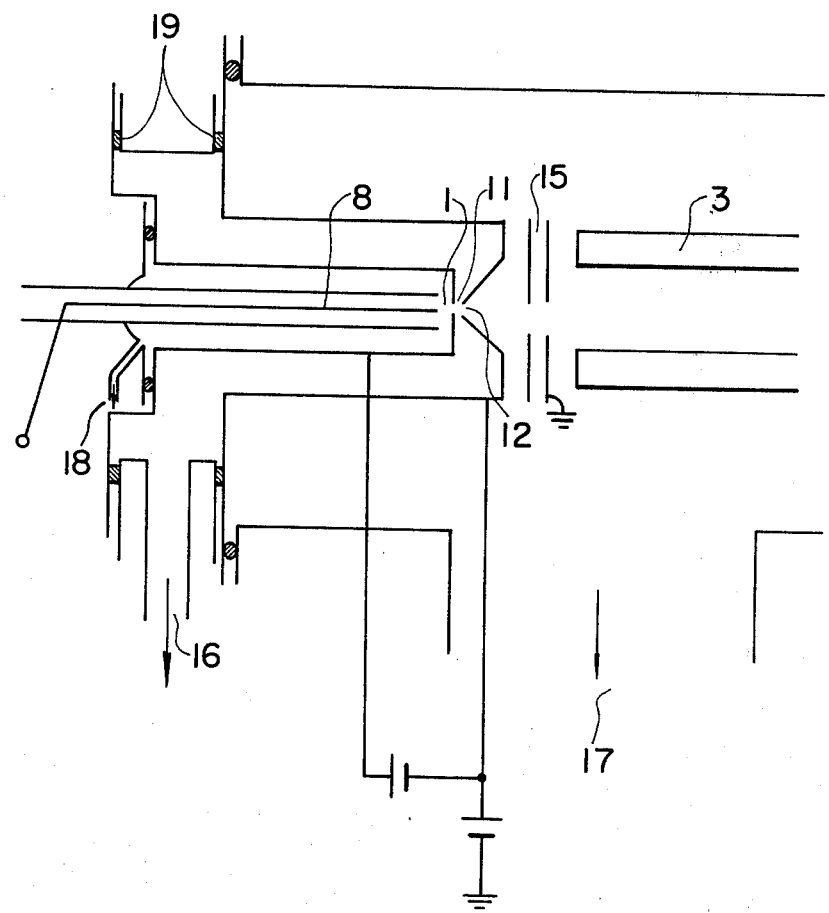

Referring to FIG. 6 which shows another embodiment, the mediate pressure region projects deeply into the mass spectrometer and pumping region, so that the gas introduced through the fine aperture 12 may be efficiently pumped out. This arrangement is superior in that the ion decompositions by ion-molecule collisions in the analysis region and the change in ion-acceleration energy because of those collisions are restrained. In FIG. 6, the reference numeral 16 denotes a port for connecting the mediate pressure region to evacuation means, while the numeral 17 designates a port for connecting the spectral region, i.e. the region where the analysis is performed, to the evacuation means. A carrier gas outlet port and an insulating gasket are designated, respectively, at numerals 18 and 19.

In the mass spectrometer of the invention, the distance between the gas jetting fine aperture 11 and the gas introducing fine aperture 12 is preferably about 0.5 to 20 mm, and optimumly 0.5 to 2.0 mm for ensuring a good performance of the jet separator.

Although the distance of 2.0 to 20 mm deteriorates the performance of the jet separator, this range of distance on the other hand provides a remarkable effect as will be described below.

When the mass spectrometer is used in the atmospheric pressure ionization mode, various complicated ions are formed. These ions are of the type having a mass number of m+1 when the original element has a mass number of m, cluster ions with reactant ions, and the like. Thus, it is difficult to discriminate the original ions from these by-product ions. In this connection, it is recalled that the dissociation energy of cluster ions is relatively small, typically 1 eV or less. Thus, when the cluster ions are accelerated by the electric field under a vacuum of a1 to 10 Torr, they collide with the neutral molecules of gases, so that the acceleration energy is conveniently changed to the internal energies of the cluster ions which are effective to dissociate the cluster ions from the ions of lower degree. Therefore, by maintaining the aforementioned distance at 2 to 20 mm, preferably 4 to 10 mm, it becomes possible to determine the original element from the observed cluster ions, which greatly contributes to the analysis. In addition, it becomes possible to assume the dissociation energy of the cluster ions.

Figure 7:
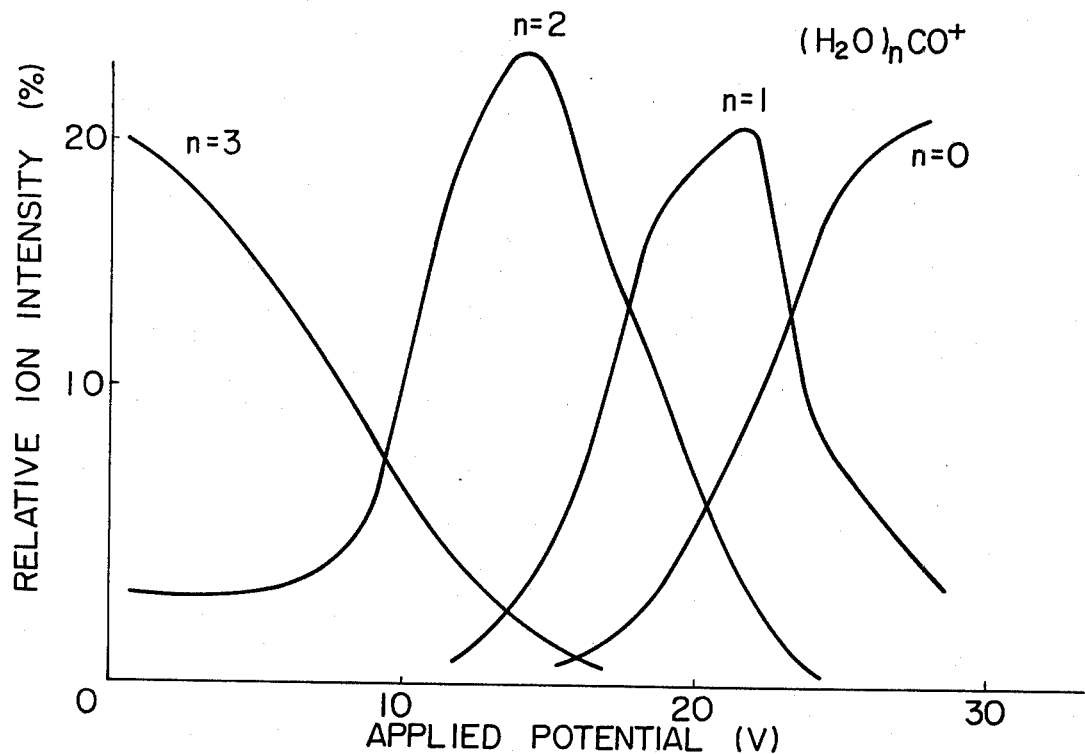
FIGS. 7 and 8 are graphs for explaining the advantages of the use of the spectrometer in accordance with the present invention.
Figure 8:
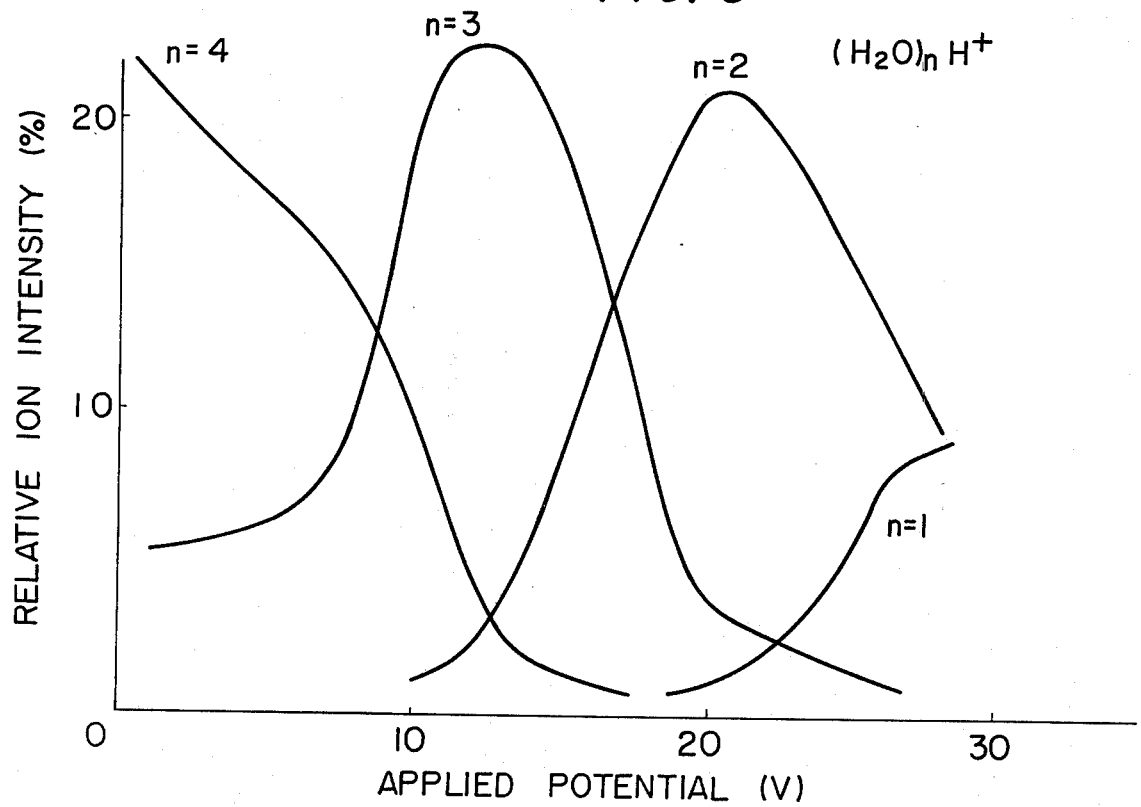

FIG. 7 and 8 show results of the analysis carried out employing the mass spectrometer of the present invention. The distance between the fine apertures was adjusted to 9mm, while the pressure at the mediate region was kept at about 1 Torr. A sample was used consisting of wet nitrogen gas containing a small amount of CO, at room temperature.

The sorts of cluster ions observed were found to change as the intensity of the electric field was changed. When the intensity of the electric field is relatively low, ions of 73 a.m.u. and 82 a.m.u. are observed. It is quite difficult to judge from this spectrum what the ions are. However, by gradually strengthening the electric field, the ions are successively dissociated and finally become $CO^+$ and $H_3O$ of 28 a.m.u. and 19 a.m.u., respectively.

As have been described, the present invention overcomes the problem of clogging of the fine aperture, which clogging has inevitably occured in conventional mass spectrometers, and provides an efficient ionization of substances having high ionization potentials and substances which are less likely to perform an ionization reaction, thereby to ensure an enhanced sensitivity of detection.

What is claimed is:

1. An atmospheric pressure ionization mass spectrometer comprising an ionization region maintained at about atmospheric pressure for ionizing a sample, a mediate pressure region maintained at about 0.1 to 10 Torr and a highly evacuated mass spectral region provided at its upstream side with auxiliary ionization means, a first partition wall separating said ionization region and said mediate pressure region for each other, at least a part of said partition wall being made of a conductive material to form a first electrode, a first fine aperture formed in said first electrode for effecting communication of said ionization region and said mediate pressure region with each other, a second partition wall separating said mediate pressure region and said mass spectral region from each other, at least a part of said second partition wall being formed of a conductive material to form a second electrode, a second fine aperture formed in said second electrode for effecting communication of said mediate pressure region and said mass spectral region with each other, said fine apertures in combination forming a jet separator, and means for applying an electric potential between said first and second electrodes.

2. A mass spectrometer as claimed in claim 1, wherein the distance between said first and second fine apertures is about 0.5 to 20 mm.

3. A mass spectrometer as claimed in claim 2, wherein said distance is about 0.5 to 2 mm.

4. A mass spectrometer as claimed in claim 2, wherein said distance is about 2 to 20 mm.

5. A mass spectrometer as claimed in claim 4, wherein said distance is about 4 to 10 mm.

6. A mass spectrometer as claimed in claim 1, wherein said auxiliary ionization means is of the electron impact type.

7. A mass spectrometer as claimed in claim 1, wherein said ionization region is kept almost at atmospheric pressure.

8. A mass spectrometer as claimed in claim 1, wherein said mediate pressure region is kept at about 0.1 to 10 Torr.

9. A mass spectrometer as claimed in claim 1, wherein said ionization means in said ionization region is of the corona discharge type.

10. A mass spectrometer as claimed in claim 1, wherein said ionization means in said ionization region is of the radioisotope type.

11. A mass spectrometer as defined in claim 1, wherein said first and second fine apertures are 60 micrometers and 200 micrometers, respectively.

* * * * *